United States Patent [19]

Fischer

[11] Plant 5,087

[45] Aug. 16, 1983

[54] AFRICAN VIOLET NAMED DARK PRINCE

[75] Inventor: Arnold W. Fischer, Hanover, Fed. Rep. of Germany

[73] Assignee: Pan American Plant Company, Parrish, Fla.

[21] Appl. No.: 252,614

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet cultivar distinguished by its very double, wine-red flowers which have up to seven petaloids. This new plant is also distinguished by its compact rosette form, its vigorous growth habit and its very good keeping qualities.

4 Drawing Figures

BACKGROUND OF THE NEW PLANT

This new African Violet cultivar originated as a seedling of unknown parentage growing in a field of violet plants maintained at Fallbrook, Calif., for breeding purposes. This plant was discovered by me at Fallbrook in 1977 and because of its unusual wine-red flowers and its apparently excellent horticultural characteristics, I selected this plant for propagation and test and I reproduced the discovery plant, by means of cuttings, at Fallbrook with favorable results. Subsequently, this new plant was propagated through several successive generations which demonstrated that the novel characteristics of the plant hold true from generation to generation and appeared to be firmly fixed. This cultivar is now being propagated on a commercial scale at West Chicago, Ill., and at Parrish, Fla.

DESCRIPTION OF THE DRAWINGS

This new violet plant is illustrated by the accompanying drawings, of which Sheet 1 is a photographic view of a potted plant in full bloom, Sheet 2 is an enlarged face view of a blossom of this plant which has been hand-painted to show the true flower color, and Sheets 3 and 4 are prints of machine copies of the front and back sides, respectively, of typical leaves of this plant.

DESCRIPTION OF THE NEW PLANT

The following is a detailed description of this new African Violet plant based upon observations made in greenhouse at West Chicago, Ill., the color designations having been made according to The R.H.S. Colour Chart published by The Royal Horitcultural Society of London, England.

THE PLANT

Origin: Seedling.
Parentage: Unknown.
Classification:
- *Botanic.*—*Saintpaulia ionantha.*
- *Commercial.*—African Violet.

Form: Compact and of rosette shape.
Growth: Strong and vigorous.
Growth rate: Rapid.
Foliage:
- *Quantity.*—Abundant, with about 25 leaves.

- *Size of leaf.*—Length — From insignificant to about 80 mm. Width — From insignificant to about 80 mm.
- *Shape of leaf.*—Oval with acute tip, cordate base and repand margins.
- *Texture.*—Pubescent.
- *Aspect.*—Glossy.
- *Color.*—Upper Side — 137A. Under Side — 138D. Edges fade into areas of 66D.
- *Ribs and veins.*—Pinnate.
- *Petioles.*—Length — From insignificant to about 80 mm.

THE BUD

Form: Globular.
Size: Average, with various diameters and lengths.
Opening rate: Typical violet.
Color of petals:
- *When sepals first divide.*—74D.
- *When petals begin to unfurl.*—72A.

Sepals:
- *Number.*—Five.
- *Shape.*—Lanceolate and branched.
- *Color.*—Inside — 199A. Outside — 199A.
- *Striae.*—None.

Calyx:
- *Size.*—Small.
- *Shape.*—Calyx splits to star shape.
- *Aspect.*—Hairy.

Peduncle:
- *Character.*—Erect and rigid.
- *Length.*—From insignificant to about 87 mm.
- *Aspect.*—Hairy.
- *Color.*—199A.

THE FLOWER

Blooming habit: Intermittent.
Flowering: Profusely.
Flower size: Medium.
- *Diameter.*—About 30 to 40 mm.
- *Depth.*—Flat.
- *Borne.*—As a cyme.
- *Shape.*—Cup-shaped when bloom first opens, becoming flat when the bloom matures.

Petalage:
- *Number of petals.*—Five.
- *Arrangement.*—Sympetalous.

*Form.*—Rotate-zygomorphic with rounded apex and repand margins.
*Texture.*—Soft.
*Appearance.*—Satiny.
*Color.*—Petal Body — 72A, becoming 74C toward the base.

Petaloids:
*Number.*—Five to seven.
*Size.*—Various.

Flower stem:
*Length.*—From insignificant to about 87 mm.
*Character.*—Strong and upright.
*Color.*—199A.

Persistence: The flowers hang on and dry.
Fragrance: None.
Lasting quality: 10 to 20 days on the plant.

REPRODUCTIVE ORGANS

Stamens:
*Anthers.*—Number: Four. Arrangement: Monadelphous. Size: About 3 mm. square. Color: Yellow.

*Filaments.*—Length: About 3 mm. Color: Whitish yellow.
*Pollen.*—Color — Yellow.

Pistils:
*Number.*—One.
*Styles.*—Length: About 5 mm. Color: 72A.
*Stigma.*—Color — Whitish.

Ovaries: Hypogynous and tomentose.

This new African Violet cultivar is distinguished by its vigorous growth, profusion of blooms and medium green foliage. The wine-red flowers are very double and appear in a cluster high above the foliage mass. This plant also has good substance and excellent keeping qualities.

I claim:

1. A new and distinct African Violet cultivar, substantially as herein shown and described, characterized by its profuse production of very double wine-red flowers of medium size having up to seven petaloids.

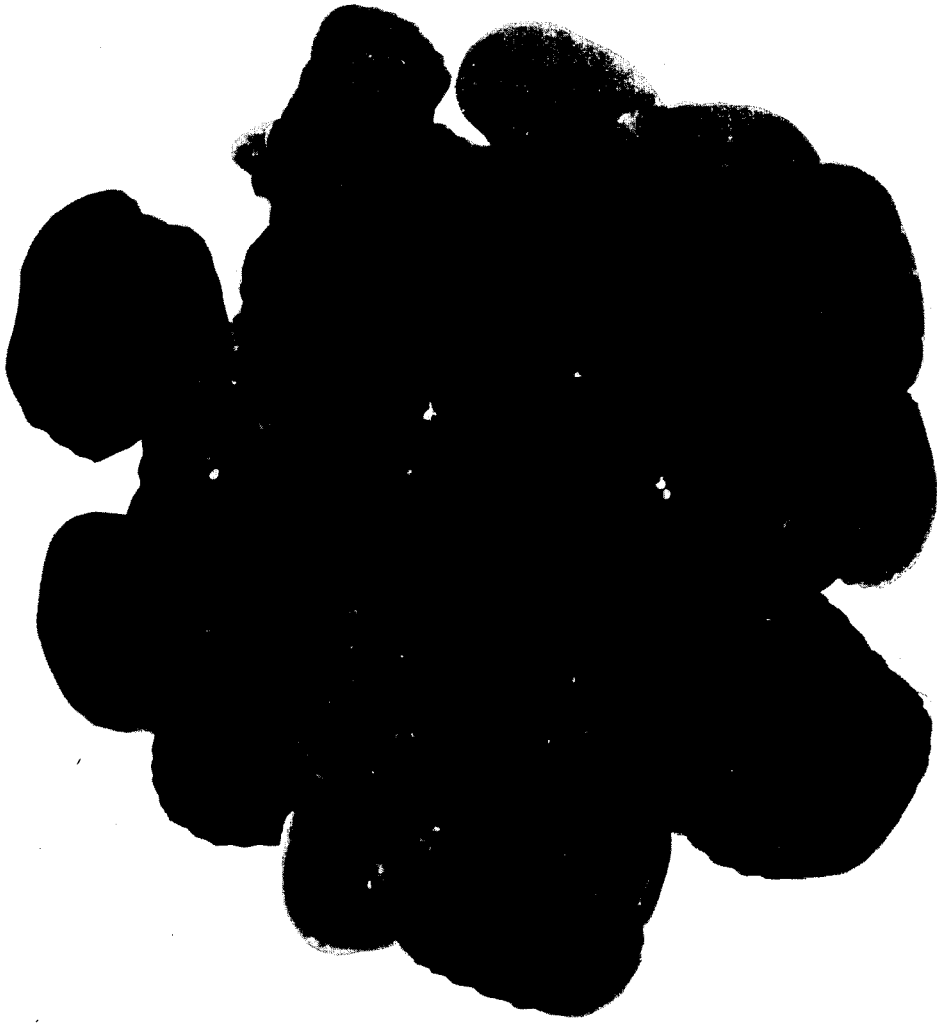

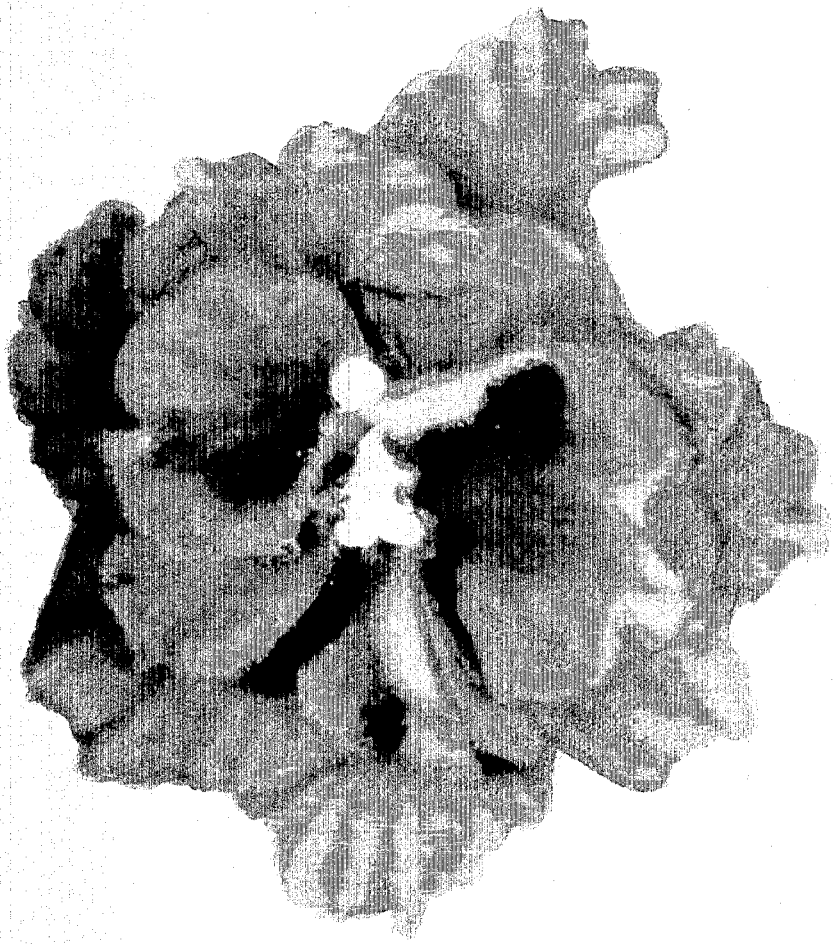

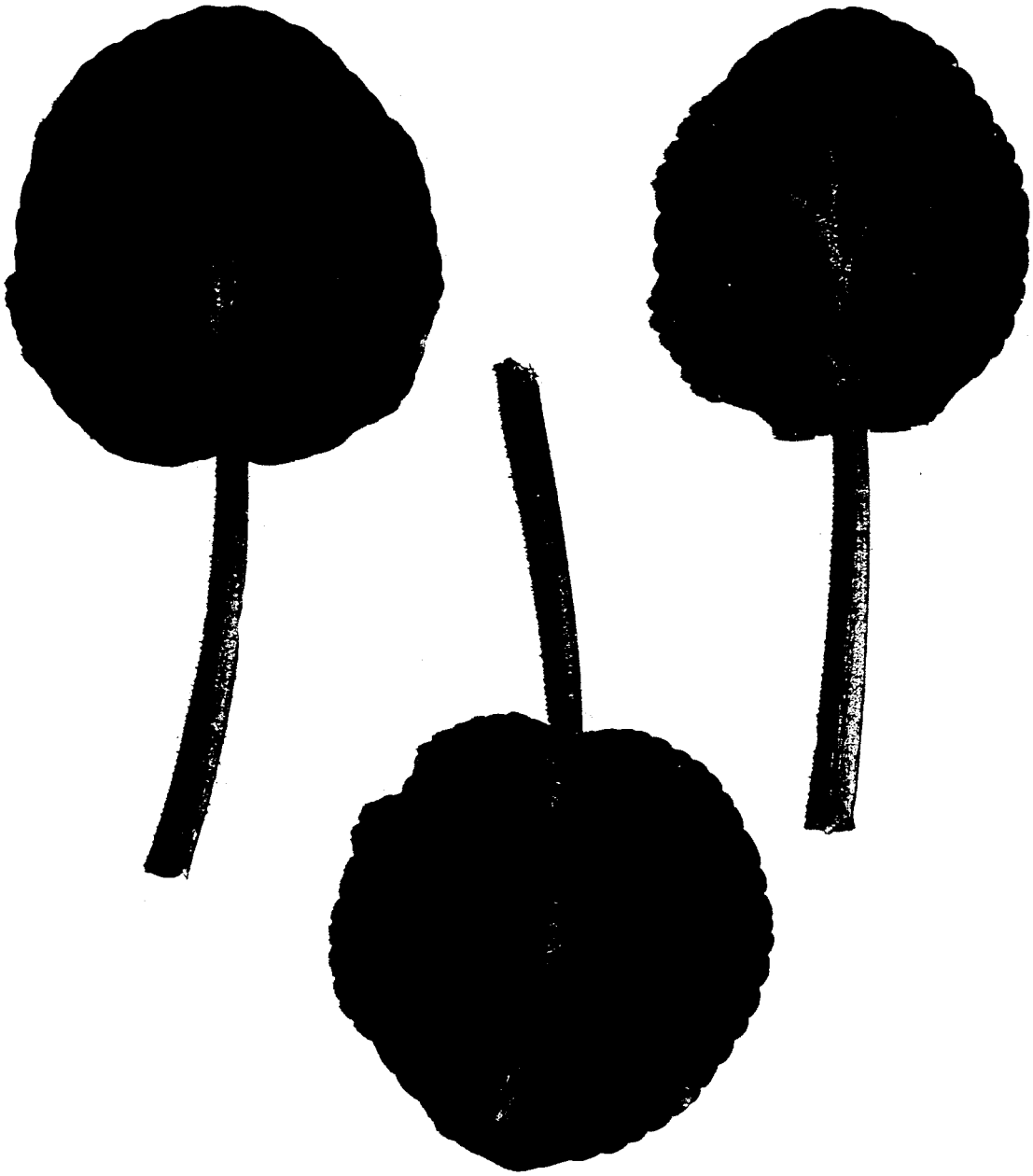

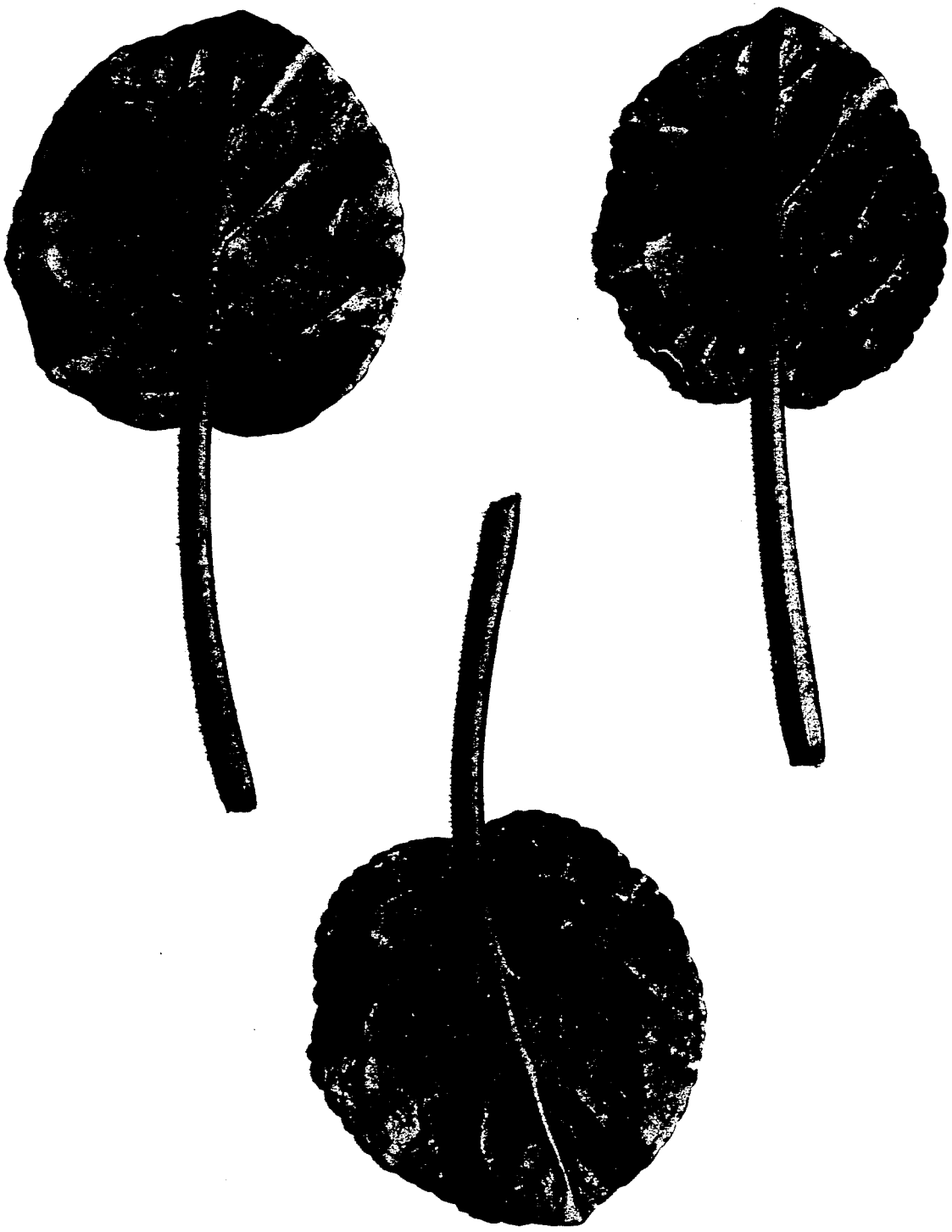

* * * * *